United States Patent [19]
Gilbert

[11] 3,956,409
[45] May 11, 1976

[54] PROCESS FOR PURIFYING TNT
[75] Inventor: Everett E. Gilbert, Morristown, N.J.
[73] Assignee: The United States of America as represented by the Secretary of the Army, Washington, D.C.
[22] Filed: June 10, 1975
[21] Appl. No.: 585,735

[52] U.S. Cl. ............................... 260/645; 260/701
[51] Int. Cl.² ......................................... C07C 79/10
[58] Field of Search ..................................... 260/645

[56] References Cited
OTHER PUBLICATIONS
Urbanski, Chemistry and Technology of Explosives, Vol. I, The MacMillan Company, New York, 1964, pp. 308 and 332 to 335.

Primary Examiner—Leland A. Sebastian
Attorney, Agent, or Firm—Nathan Edelberg; Robert P. Gibson; A. Victor Erkkila

[57] ABSTRACT

Unsymmetrical TNT isomers are removed from solid or molten crude TNT by treatment with aqueous ammonium sulfite. The yield of purified TNT is significantly greater by treatment with aqueous ammonium sulfite than with conventional sodium sulfite ("sellite") at acceptable levels of isomer removal. By use of ammonium bisulfite together with ammonium sulfite or operation in a closed system to avoid loss of ammonia, high yields of TNT with essentially complete removal of TNT isomers can be obtained at low sulfite levels.

8 Claims, No Drawings

PROCESS FOR PURIFYING TNT

GOVERNMENTAL INTEREST

The invention described herein may be manufactured, used and licensed by or for the Government for governmental purposes without the payment to me of any royalty thereon.

BACKGROUND OF THE INVENTION

TNT (2,4,6-trinitrotoluene, also called $\alpha$TNT), as conventionally manufactured by nitration processes from toluene and mixed acid as starting materials, contains significant proportions (usually about 4%) of undesired, unsymmetrical isomers. The standard industrial procedure for removing these isomeric impurities is to treat the crude TNT with aqueous sodium sulfite ("sellite"), which reacts with the reactive nitro groups in the meta or 3-position and produces a waste sellite solution containing a mixture of sodium 2,4-dinitrotoluene-3 and -5 sulfonates.

SUMMARY AND DETAILED DESCRIPTION OF THE INVENTION

An object of the present invention is to provide a novel and efficient process for removing unsymmetrical TNT isomers from TNT.

Another object of this invention is to provide a process for purifying crude TNT, whereby a superior recovery of TNT with complete removal of TNT isomers can be achieved.

A further object is to provide a more economical process for purifying TNT than with standard "sellite".

A still further object is to provide a process for purifying TNT, whereby the pollution problem attending the purification of crude TNT can be reduced or substantially eliminated. Other objects will become apparent as the invention is further described.

In accordance with the process of the present invention, the foregoing and other objects can be achieved when TNT containing unsymmetrical isomeric impurities is contacted with an aqueous solution of ammonium sulfite, preferably in mixture with ammonium bisulfite.

As far as is known, the use of ammonium sulfite has not been considered for purifying TNT, although ammoniacal sodium sulfite solution has been employed for that purpose. However, in such use the ammonium hydroxide was employed for the purpose of neutralizing the acidity present in the acid TNT, thereby eliminating the necessity for fresh water washing of the acid TNT oil, since the free ammonia neutralized the acid in the crude oil. (Raifsnider, P. J., "New Techniques Improve TNT Manufacture", Chemical Industries, 57, 1054-6 (1945); Clear, A. J. and Rinkenbach, W. H. "The Use of Ammoniacal Sellite For The Purification Of TNT", Picatinny Arsenal Technical Report, June 24, 1944).

The process of the present invention comprises mixing solid or molten crude TNT containing unsymmetrical TNT isomers with an aqueous solution consisting essentially of ammonium sulfite at temperatures below as well as above the melting point of the crude TNT, e.g. from about 20°C. to 100°C. During the process, the ammonium sulfite reacts with the reactive meta nitro groups, thereby converting the unsymmetrical isomers into ammonium 2,4-dinitrotoluene-3 and -5 sulfonates, which are soluble in the aqueous solution and thus can be separated from the insoluble, purified TNT. When solid crude TNT is employed in the process, it is desirable to utilize the TNT in finely divided form, and advantageously to carry out the process in an apparatus, such as a ball mill, containing grinding and/or attrition elements, which continuously comminute the TNT particles and/or expose fresh surfaces thereof to the aqueous sulfite solution, and thereby optimize the purification reaction.

The amount of ammonium sulfite employed depends principally on the amount of unsymmetrical TNT isomers present in the crude TNT, and the degree of purification desired, and to a lesser extent on such factors as the concentration of sulfite solution and time and temperature of the reaction. Generally, the ammonium sulfite is employed in an amount not greatly exceeding that required to react with and remove the unsymmetrical TNT isomers so as to minimize the reaction thereof with TNT and consequent loss of yield of purified TNT.

The following reactions are believed to take place during the purification of impure TNT with ammonium sulfite according to the present invention.

The principal reaction occurring during conventional purification of TNT with sodium sulfite is as follows:

$$RNO_2 + Na_2SO_3 \rightarrow RSO_3Na + NaNO_2 \quad (1)$$

A similar reaction occurs with ammonium sulfite, viz.

$$RNO_2 + (NH_4)_2SO_3 \rightarrow RSO_3NH_4 + NH_4NO_2 \quad (2)$$

However, ammonium nitrite reacts readily with sulfites in a series of reactions, the first of which is probably as follows:

$$NH_4NO_2 + 3(NH_4)_2SO_3 \rightarrow 4NH_3 + N(SO_3NH_4)_3 + 2H_2O \quad (3)$$

Adding equations (2) and (3) gives:

$$RNO_2 + 4(NH_4)_2SO_3 \rightarrow RSO_3NH_4 + 4NH_3 + N(SO_3NH_4)_3 + 2H_2O \quad (4)$$

Depending on the pH, the triammonium nitrilotrisulfonate can undergo stepwise hydrolysis, viz.:

$$N(SO_3NH_4)_3 + H_2O \rightarrow NH(SO_3NH_4)_2 + NH_4SO_4H \quad (5)$$

$$NH(SO_3NH_4)_2 + H_2O \rightarrow NH_2SO_3NH_4 + NH_4SO_4H \quad (6)$$

$$NH_2SO_3NH_4 + H_2O \rightarrow (NH_4)_2SO_4 \quad (7)$$

By adding equations (5), (6) and (7), and neutralizing with the $NH_3$ liberated in equation (3), there is obtained:

$$N(SO_3NH_4)_3 + 3H_2O + 2NH_3 \rightarrow 3(NH_4)_2SO_4 \quad (8)$$

The overall reaction is as follows:

$$RNO_2 + 4(NH_4)_2SO_3 + H_2O \rightarrow RSO_3NH_4 + 2NH_3 + 3(NH_4)_2SO_4 \quad (9)$$

Equations (4) and (9) are both consistent with the observed formation of ammonia during the purification treatment with ammonium sulfite. Also, they both require the comsumption of four moles of ammonium sulfite per mole of unsymmetrical TNT isomers, corresponding to 14 millimoles of ammonium sulfite for 88 millimoles of crude TNT containing 4% of such isomers. In this connection it is noted from Table 3 below that the observed "break point" is between 10.8 and 16.2 millimoles.

As indicated by the foregoing reactions, ammonia is generated in the purification reaction. Thus, when the process is performed in an open system, the ammonia generated in the reaction is evolved, which results in a reduction in the pH of the sulfite solution, e.g. about from 9 at the beginning to about 2 at the end, thereby requiring larger amounts of ammonium sulfite to accomplish a desired degree of purification. However, it has been found that by carrying out the process so as to prevent or minimize the loss of ammonia from the system, a complete removal of unsymmetrical TNT isomers together with high yields of purified TNT can be achieved with relatively small proportions of ammonium sulfite.

A preferred embodiment of the present invention comprises carrying out the process using ammonium bisulfite in mixture with ammonium sulfite. In such process the ammonium bisulfite apparently reacts with the ammonia generated in the the reaction and prevents loss of ammonia from the system. More specifically by effecting the process with an aqueous mixture of ammonium sulfite and ammonium bisulfite, beginning at a slightly acid pH, e.g. about 6–6.5, no ammonia is evolved and the pH of the aqueous solution at the end of the purification process has decreased to about 1, even when operating in a closed system. It has been unexpectedly found that by carrying out the process in this manner with a mixture of ammonium sulfite and ammonium bisulfite, high yields of TNT with essentially complete removal of TNT isomers can be obtained at low total sulfite levels and without the need for operation in a closed system. The amount of ammonia reacted in this manner depends on the ratio of ammonium bisulfite to sulfite employed. Theoretically, the ammonia formed in the purification reaction is completely neutralized and converted to ammonium sulfite when equimolecular proportions of ammonium sulfite and ammonium bisulfite are used, as shown by the following equation:

$RNO_2 + 2(NH_4)_2SO_3 + 2NH_4HSO_3 + H_2O \rightarrow RSO_3NH_4 + 3(NH_4)_2SO_4$ Even under such conditions ammonia can be liberated to some degree by secondary reactions, e.g. hydrolysis of the ammonium sulfate formed, and lost by evaporation along with water, so that it may be desirable for optimun results to operate in a closed system or with a reflux condenser to inhibit such loss.

Although ammonium bisulfite reacts with the unsymmetrical TNT impurities in similar manner, as shown by the following theoretical reaction:

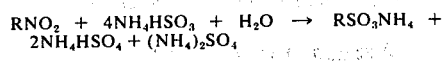

$RNO_2 + 4NH_4HSO_3 + H_2O \rightarrow RSO_3NH_4 + 2NH_4HSO_4 + (NH_4)_2SO_4$ such reaction is too slow for practical use. Generally, when mixtures of $(NH_4)_2SO_3$ and $NH_4HSO_3$ are employed in the process of the present invention, at least about 0.3 mol and preferably at least about 1 mol of $(NH_4)_2SO_3$ per mol of $NH_4HSO_3$ are utilized.

The TNT to be purified according to the present process is preferably washed with water and/or aqueous alkaline solution to remove small amounts of acid, notably sulfuric and nitric acids, usually adhering thereto during manufacture. If crude TNT containing small amounts of such adhering acid is utilized as starting material, the acid can be neutralized by means of a base, such as ammonium hydroxide, incorporated in the ammonium sulfite solution; or the acid can be neutralized by the ammonium sulfite employed, thereby forming a mixture of ammonium sulfite and ammonium bisulfite suitable for use in the present process.

The following examples illustrate specific embodiments of the method of carrying out the process of the present invention.

EXAMPLES

The crude TNT employed in all of the following examples was obtained from the Radford Army Ammunition Plant, in Radford, Virginia. Prior to its use in the examples, it was subjected to a series of melt-washes with water at 80°–82°C. until the washes were of neutral pH. The crude TNT washed in this manner had the following content of unsymmetrical TNT isomers (determined by gas chromatography) shown in Table 1. The table also shows a total content of 0.123% of unsymmetrical TNT isomers of a typical Radford finished TNT product obtained by standard sellite purification.

Table 1

| Isomeric TNT | Crude TNT % | Radford Finished TNT % |
|---|---|---|
| 2,3,5 | 0.159 | 0 |
| 2,4,5 | 2.61 | 0.042 |
| 2,3,4 | 1.48 | 0.081 |
| TOTAL | 4.25 | 0.123 |

Purification With $(NH_4)_2SO_3$ In An Open System

EXAMPLES 1–10

20 grams (88 millimoles) of crude TNT were stirred into a predetermined amount of an aqueous solution containing 12.5 wt. % of anhydrous ammonium sulfite in an open vessel at 80°–82°C. The two phase emulsion thus obtained was heated with vigorous agitation for 10, 20 or 30 minutes. The mixture was then cooled and the spent sulfite solution was separated by decantation from the solidified TNT. The TNT thus obtained was melt-washed by agitating it with 100 ml. of water at 80°C., cooling and separating the solidified TNT from the wash liquor. The procedure was repeated three times until the wash was of neutral pH. The purified TNT was dried and then analyzed for content of unsymmetrical TNT isomers.

Comparison runs were carried out in the same manner with an aqueous solution containing 14.5 wt. % sodium sulfite. In the experiments with both the ammonium and sodium sulfite solutions, various ratios of TNT to sulfite were employed.

The experimental results are summarized in Table 2. As is evident, there is considerable scatter in the data. This scatter is not attributed to the analytical procedure, since duplicate determinations were always within five percent. On the contrary the scatter is probably due to uncontrollable variations, e.g. temperatures, stirring rate, from one experiment to another. However, the data to allow a qualitative comparison between the effectiveness of the two reagents in the open system.

It is evident from Table 2 that ammonium sulfite effectively removed the unsymmetrical TNT isomers to a level below the Radford level of 0.123%. Thus, for every 88 millimoles of crude TNT treated approximately 86 millimoles of anhydrous ammonium sulfite were required as compared to 46 millimoles of standard sodium sulfite, corresponding to 0.5 pound of ammonium sulfite and 0.29 pound of sodium sulfite for each pound of crude TNT, resp. Further, a shown in Table 2, while considerably more ammonium sulfite than sodium sulfite was required to accomplish the removal of unsymmetrical TNT isomers, a significantly greater recovery of purified TNT was obtained when ammonium sulfite was employed. Thus, at the Radford level of 0.123% of unsymmetrical TNT isomers noted above (attained with 46 millimoles/30 min. for $Na_2SO_3$ and 86 millimoles/20 min. for $(NH_4)_2SO_3$, see example 9 and 6 resp.), the recovery of TNT was 64% for sodium sulfite and 81% for ammonium sulfite - a difference of 17%.

internal standard (p-nitrotoluene) using previously determined correction factors.

*Dexsil 300 GC is a silicone polymer containing meta carborane units, sold by Olin Corp.
** Anakrom is a diatomaceous earth gas chromatography support sold by Analabs, Inc., New Haven, Conn.

Purification With $(NH_4)_2SO_3$ And Retention of Ammonia In The System

EXAMPLES 11–15

During operation in an open system, as illustrated in the foregoing examples, it was noted that the pH of the sodium sellite liquor remained essentially constant throughout the purification reaction, while the pH of the ammonium sulfite liquor dropped to 2–3 as ammonia was evolved.

The following examples illustrate the purification treatment with ammonium sulfite under conditions Table 2

Purification of TNT Using $(NH_4)_2SO_3$ or $Na_2SO_3$ In An Open System[1]

| Ex. | Weight Ratio TNT: Sulfite Solution[2] | m moles | | Time, Min. 10 Unsym. Isomers, % | 20 | 30 | Time, Min. 10 TNT Recovery, % | 20 | 30 |
|---|---|---|---|---|---|---|---|---|---|
| 1 | 1:0.75 | 16.2 | $(NH_4)_2SO_3$* | 2.07 | 2.14 | 2.02 | 95.1 | 95.0 | 94.8 |
| 2 | 1:1.0 | 21.6 | " | 1.64 | 1.14 | 1.66 | 94.1 | 94.0 | 94.6 |
| 3 | 1:1.25 | 27.0 | " | 2.01 | 1.35 | 0.63 | 93.6 | 93.2 | 92.0 |
| 4 | 1:2.0 | 43.3 | " | 0.38 | 0.79 | 0.87 | 87.5 | 89.0 | 88.0 |
| 5 | 1:3.0 | 64.8 | " | 0.42 | 0.23 | 0.32 | 86.0 | 84.0 | 83.1 |
| 6 | 1:4.0 | 86.4 | " | 0.41 | 0.11 | 0.08 | 86.0 | 81.0 | 79.5 |
| 7 | 1:5.0 | 108 | " | 0.23 | 0.05 | 0.01 | 80.0 | 76.4 | 74.5 |
| 8 | 1:1.0 | 23 | $Na_2SO_3$* | 0.86 | 0.80 | 0.23 | 84.3 | 82.8 | 81.0 |
| 9 | 1:2.0 | 46 | " | 0.68 | 0.18 | 0.07 | 71.0 | 66.6 | 64.0 |
| 10 | 1:3.0 | 69 | " | 0.27 | 0.85 | 0.07 | 59.0 | 54.7 | 51.0 |

Notes:
[1]Temperature = 80°C.
[2]TNT = 20.0g (88 mmole)
*12.5 wt. % $(NH_4)_2SO_3$ and 14.5 wt. % $Na_2SO_3$ solutions.

The purified TNT products were analyzed by gas chromatography as follows:

Samples were prepared by dissolving a weighed quantity to volume with acetone (usually 0.2g. per ml). Aliquots of 5 microliters were chromatographed on a 9 foot × ⅛ inch stainless steel column packed with 8% Dexsil 300 GC* on Anakrom**. The chromatograph was a model 188 Varian Aerograph equipped with flame ionization detectors. The carrier gas was helium at a flow rate of 50 ml/min. The flame was fed with hydrogen at a flow rate of 50 ml/min., and zero air at a flow rate of 500 ml/min. The injection port temperature was 225°C., the detector temperature 265°C. The column was programmed from 110°C. to 225°C. at a rate of 8°/min. for 14.4 minutes and then run isothermally at 225°C. until all peaks were eluted (approximately 20 minutes). The areas under the peaks were integrated with a Varian model 480 integrator and the percentage isomers calculated by normalizing to an which essentially prevented loss of ammonia during the reaction and thereby maintained the system at essentially constant pH. All runs were conducted at 80°–85°C. for 30 minutes with 88 millimoles of crude TNT in a sealed glass vessel using a magnetic stirrer except for example 14, wherein a reflux condenser open to the atmosphere was used. The results are summarized in Table 3 together with those of corresponding runs made in an "open" system summarized in Table 2.

As shown in the Table, surprisingly advantageous results were obtained when ammonia was retained in the system, since complete removal of unsymmetrical isomers was achieved thereby at very low levels of ammonium sulfite. Examples 13 and 14 are of particular interest, since they yielded 94–96% recoveries of purified TNT with complete removal of isomers. Also, it is interesting to note that the melting points of the purified TNT products optained in the "closed" system were 0.5° to 1.0°C. higher than those of the TNT products obtained in the "open" system.

Table 3

Treatment with Retention of Ammonia

| Example | $(NH_4)_2SO_3$ (mmoles) | Final pH Closed | Open[2] | Yield (%) Closed | Open[2] | Unsym.TNT(%) Closed | Open[2] | M.p.[3]°C. Closed | Open[2] |
|---|---|---|---|---|---|---|---|---|---|
| 11 | 43.3 | 9.4 | 3 | 85 | 88 | 0 | 0.87 | 80 | 79.5 |
| 12 | 21.6 | — | — | 91 | 95 | 0 | 1.66 | 80 | 79.0 |
| 13 | 16.2 | — | 2.3 | 96 | 95 | 0 | 2.02 | 79.5 | 78.5 |
| 14[1] | 16.2 | 9.0 | 2.3 | 94 | 95 | 0 | 2.02 | 79.0 | — |
| 15 | 10.8 | 8.9 | — | 95 | — | 0.28 | — | — | — |

Notes:
[1]In example 14, using a reflux condenser, no odor of ammonia was noted at the top of the condenser. However, some ammonia was

Table 3-continued

| Example | $(NH_4)_2SO_3$ (mmoles) | Treatment with Retention of Ammonia | | | | | | | |
|---|---|---|---|---|---|---|---|---|---|
| | | Final pH | | Yield (%) | | Unsym.TNT(%) | | M.p.[3]°C. | |
| | | Closed | Open[2] | Closed | Open[2] | Closed | Open[2] | Closed | Open[2] | actually being evolved, as shown by the reaction of moist pH paper. The pH of the system can be controlled by maintaining control of the quantity of ammonia permitted to escape during the purification treatment.
[2]"Open" runs reported in Table 2.
[3]Uncorrected, run in capillary tubes in a Thomas-Hoover apparatus.

Purification of Solid TNT With $(NH_4)_2SO_3$

EXAMPLE 16

2.6 grams (20 millimoles) of $(NH_4)_2SO_3.H_2O$ were added to a slurry of 20 grams (88 millimoles) of finely ground crude TNT in 26 ml. of water. The resulting mixture was heated and vigorously agitated at 55°C. for one hour. The mixture was then filtered, and the filter cake was washed with cold water and dried. 18.7 grams of purified TNT containing 0.20% total unsymmetrical TNT isomers were obtained, corresponding to a yield of 94%.

EXAMPLE 17

The foregoing example was repeated except that the mixture was agitated at 70°C. instead of 55°C. 18.3 grams of purified TNT containing 0.18% of total unsymmetrical TNT isomers were obtained, corresponding to a yield of 92%.

Purification With Mixtures of Ammonium Sulfite and Ammonium Bisulfite

EXAMPLE 18

Use of $(NH_4)_2SO_3$ and $NH_4HSO_3$ in 1:1 Molar Ratio.

A mixture of 20 (88 millimoles) of crude TNT, 1.3 grams (10 millimoles) of $(NH_4)_2SO_3.H_2O$, 1 gram (10 millimoles) of $(NH_4)_2HSO_3$ and 16 ml. of water was vigorously agitated at 85°C. for 30 minutes in a sealed container. The mixture was then allowed to cool and the solidified TNT was separated from the aqueous liquor by filtration. The purified TNT thus obtained was melt-washed twice at 80°–85°C. with two successive 100 ml. portions of pure water and dried. 18.9 grams (95% yield) of purified TNT containing 0.30% total unsymmetrical TNT isomers were obtained.

EXAMPLE 19

Use of $(NH_4)_2SO_3$ and $NH_4HSO_3$ in 3:1 Molar Ratio.

A mixture of 20 grams (88 millimoles) of crude TNT, 2.0 grams (15 millimoles) of $(NH_4)_2SO_3.H_2O$, 0.5 gram (5 millimoles) of $NH_4HSO_3$ and 15.6 ml. of water was vigorously agitated at 85°C. in a flask equipped with a reflux condenser. During this period the pH of the reaction mixture was 6 initially and 8 at the end, and an odor of ammonia was noted at the end of the reflux condenser. The mixture was then cooled and the solidified TNT was separated, melt-washed with water and dried as in example 18. 19.0 grams (95% yield of purified TNT containing 0.20% total unsymmetrical TNT isomers were obtained.

EXAMPLE 20

Use of $(NH_4)_2SO_3$ and $NH_4HSO_3$ in 2:1 Molar Ratio

A mixture of 20 grams (88 millimoles) of crude TNT, 2.0 grams (20 millimoles) of $NH_4SO_3H$, 0.22 gram (13 millimoles of $NH_3$ and 18 ml. of water was vigorously agitated at 85°C. for 30 minutes in a flask equipped with a reflux condenser. During this period the pH of the reaction mixture was 6.4 initially and 1.0 finally. The mixture was cooled and the solidified TNT was separated, melt-washed with water and dried as above. 18.8 grams (94% yield) of purified TNT was obtained.

Economic Advantages of Purification with Ammonium Sulfite

As shown in Table 3, 16.2 mmoles of $(NH_4)_2SO_3$ (as 12.5% aqueous solution) are required under laboratory conditions to purify 88 mmoles of TNT containing 4% isomeric impurities, which corresponds with 0.094 lb. of $(NH_4)_2SO_3$ (0.75 lb. of 12.5 wt. % aqueous solution) per pound of TNT, as compared with approximately 0.3 lb. of $Na_2SO_3$ per pound of TNT. When the same crude TNT is purified with aqueous $Na_2SO_3$ under conventional plant conditions, 0.09 lb. $Na_2SO_3$ per pound of TNT is required. Thus, in view of the much lower cost of ammonium sulfite and considering only the raw material costs without recycle (recovery) of waste sulfite liquor, purification with ammonium sulfite is substantially less costly than purification with sodium sulfite under plant conditions.

Various methods can be employed for the recovery of ammonium sulfate, including the ammonia and sulfur values thereof, from the waste sulfite liquor ("redwater") obtained by the ammonium sulfite process, and such recovery methods unlike the sodium selliting process, are essentially nonpolluting in that they are self-contained. For example, the waste liquor can be processed to recover its content of dinitrotoluene sulfonates as 2,4-toluenediamine according to the method described in my pending U.S. Patent Application Ser. No. 556,352, filed Mar. 7,1975, "Recovery of 2,4-Toluenediamine From Waste Sulfite Liquor Obtained In TNT Purification", and the resulting liquors can be evaporated to dryness to recover their content of ammonium sulfate. The ammonium sulfate thus obtained can be marketed, e.g. as fertilizer, or further processed to recover the $NH_3$ and $SO_2$ values thereof.

An important advantage of the ammonium sulfite purification process resides in the diversity of possible recycle methods for recovering $NH_3$ and $SO_2$ values. For example, the ammonium sulfate recovered therein can be thermally decomposed, e.g. at 400°C, viz.

H Reaction = +1099 BTU/lb. $(NH_4)_2SO_4$ (endothermic)

and the $NH_3$ and $SO_2$ obtained thereby can be recycled to form ammonium sulfite (Halstead, W. D., J. Appl. Chem., 20, 129 (1970). Alternatively, the ammonium sulfate can be heated with zinc oxide, whereby it is theoretically possible to recycle all of the $NH_3$ and $SO_2$, viz.

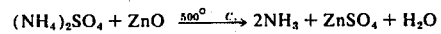

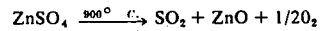

H Reaction Overall: +1,787 BTU/lb. (NH$_4$)$_2$SO$_4$ (endothermic) (W. Ger. Pat. No. 1,232,188 (1967); Ref. *Chem. Abs.* 67, 110, 204 (1967)). According to another method the ammonium sulfate can be incinerated with sulfuric acid, whereby all of the SO$_2$ is potentially recoverable and the ammonium ion is lost as nitrogen. This method has been recently developed by the industry to dispose of (NH$_4$)$_2$SO$_4$, which is a major by-product of caprolactam manufacture.

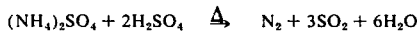

H Reaction (Net) = −277 BUT/lb. (NH$_4$)$_2$SO$_4$ (exothermic).

Assuming that the sulfuric acid must be decomposed during the recycle of spent acids in TNT manufacture, the net effect of incinerating (NH$_4$)$_2$SO$_4$ along with the spent acid is to reduce energy requirements.

The foregoing disclosure is merely illustrative of the principles of this invention and is not to be interpreted in a limiting sense. I wish it to be understood that I do not desire to be limited to exact details of construction shown and described, because obvious modifications will occur to a person skilled in the art.

What is claimed is:

1. A process for purifying 2,4,6-trinitrotoluene containing unsymmetrical trinitrotoluene isomeric impurities, which comprises reacting the impure 2,4,6-trinitrotoluene with an aqueous solution consisting essentially of ammonium sulfite to convert sais isomeric impurities into products soluble in said aqueous solution, and separating the purified 2,4,6-trinitrotoluene from the aqueous solution containing said soluble conversion products.

2. The process according to claim 1, wherein the reaction is carried out while substantially inhibiting the loss of ammonia from the system.

3. The process according to claim 1, wherein the reaction is carried out at a temperature sufficient to maintain the trinitrotoluene in molten condition.

4. The process according to claim 1, wherein the impure 2,4,6-trinitrotoluene is substantially free from acidic impurities.

5. The process according to claim 1, wherein at least about four moles of ammonium sulfite are employed per mole of such isomeric impurities.

6. The process according to claim 1, wherein the aqueous ammonium sulfite solution additionally contains ammonium bisulfite.

7. The process according to claim 6, wherein the solution contains at least about 0.3 mole of ammonium sulfite per mole of ammonium bisulfite.

8. The process according to claim 6, wherein the solution possess a pH below 7.

* * * * *